_United States Patent_ [19]

Anello et al.

[11] 4,411,843

[45] * Oct. 25, 1983

[54] CONVERSION OF 1,1,1-TRICHLOROPERHALOALKANES INTO PERHALOALKANOYL CHLORIDES

[75] Inventors: Louis G. Anello, Hamburg; Richard E. Eibeck, Orchard Park; Martin A. Robinson, East Amherst, all of N.Y.

[73] Assignee: Allied Corporation, Morris Township, Morris County, N.J.

[*] Notice: The portion of the term of this patent subsequent to Jul. 20, 1999, has been disclaimed.

[21] Appl. No.: 372,576

[22] Filed: Apr. 29, 1982

Related U.S. Application Data

[63] Continuation-in-part of Ser. No. 216,033, Dec. 15, 1980, Pat. No. 4,340,548.

[51] Int. Cl.³ ............................................. C07C 51/58
[52] U.S. Cl. ................................................ 260/544 Y
[58] Field of Search ........................ 260/544 Y, 544 F

[56] References Cited

U.S. PATENT DOCUMENTS 3,102,139  8/1963  Lawler et al. ................. 260/544 Y
3,725,475  4/1973  Paucksch et al. ............. 260/544 Y
4,340,548  7/1982  Anello et al. ................. 260/544 Y _Primary Examiner_—Natalie Trousof
_Assistant Examiner_—L. Hendriksen
_Attorney, Agent, or Firm_—Arthur J. Plantamura; Jay P. Friedenson; Thomas D. Hoffman

[57]         ABSTRACT

A process for the preparation of perhaloalkanoyl chloride is disclosed which comprises reacting 1,1,1-trichloroperfluoroalkane, with a sulfur trioxide-containing compound selected from the group consisting of oleum sulfur trioxide and stabilized sulfur trioxide in the presence of catalytic amounts of a halogen catalyst selected from the group consisting of iodine, bromine, iodine monobromide and iodine monochloride and bromine monochloride wherein the 1,1,1-trichloroperhaloalkane is a straight or branched chain acyclic organic compound having 2 to 8 carbon atoms and having at least one trihalomethyl group wherein at least one halo atom is fluorine and having the remaining carbon atoms substituted by F, Cl, Br or I atoms.

9 Claims, No Drawings

CONVERSION OF 1,1,1-TRICHLOROPERHALOALKANES INTO PERHALOALKANOYL CHLORIDES

DESCRIPTION

CROSS REFERENCE TO RELATED APPLICATION

This application is a continuation-in-part application to co-pending U.S. patent application Ser. No. 216,033, filed Dec. 15, 1980.

BACKGROUND OF THE INVENTION

The present invention relates to preparation of perhaloalkanoyl chloride by contacting 1,1,1-trichloroperhaloalkanes with a $SO_3$-containing substance in the presence of a catalytic amount of a halogen catalyst, such as bromine.

Perhalo compounds wherein the halogen is chlorine or fluorine are particularly resistant to oxidizing agents. Specifically, trifluoroacetyl chloride, $CF_3COCl$, a known chemical compound having a boiling point of $-19°$ C., is a valuable chemical intermediate, useful for the preparation of trifluoroethanol, trifluoroacetic acid, and trifluoroacetaldehyde. Trifluoroethanol, further is a raw material useful in the manufacture of novel anesthetic compounds. Perhaloalkanoic acids, such as trifluoroacetic acid is also an intermediate for the preparation of compounds useful as herbicides, insecticides, dyes, etc. Higher homologous perhaloalkanoyl chlorides, for example perfluorooctanoyl chloride, $CF_3(CF_2)_6COCl$ is easily converted to the carboxylic acid or acid salt which is useful as a surfactant.

In the relevant prior art procedures, trifluoroacetyl chloride has been prepared by the catalytic hydrolysis of 1,1,1-trifluoro-2,2,2-trichloroethane, using oleum, (sulfur trioxide dissolved in sulfuric acid), in the presence of toxic mercurial salt catalysts. These prior art procedures are described, particularly in Lawlor and Braid: U.S. Pat. No. 3,102,139; Dittman and Zager: U.S. Pat. No. 3,160,659; and Pauchsch et al.: U.S. Pat. No. 3,725,475.

Trifluoroacetyl chloride has also been previously prepared by subjecting a mixture of chlorine, oxygen and 1,1,1-trifluoro-2,2,2-trichloroethane to ultraviolet irradiation under anhydrous conditions, as described by Braid and Lawlor in U.S. Pat. No. 3,151,051.

In general, methods described in the prior art for the preparation of perhaloalkanoyl compounds have required excessively prolonged reaction times, elevated reaction pressures, hazardous ultraviolet radiation, and have generally resulted only in low yields of the desired end products, frequently accompanied by losses of starting materials due to side reactions such as carbon-to-carbon bond cleavage. In addition, the prior art preparations discussed above have also been characterized by the need to use toxic mercurial salt catalysts, which require costly environmental pollution control systems, and which create difficult environmental waste disposal problems, particularly associated with the safe disposal of by-product sulfuryl chloride-containing mercurial salts.

Thus, a process for the preparation of perhaloalkanoyl chloride from 1,1,1-trichloroperhaloalkane using a nonmetallic, nonpolluting, and low cost halogen catalyst, has significant commercial and technical value.

Accordingly it is an object of the present invention to provide a process for the preparation of perhaloalkanoyl chloride in the presence of a halogen catalyst which is non-metallic and which embodies none of the operating and environmental disadvantages of the prior art procedures.

SUMMARY OF THE INVENTION

In accordance with the objects of the present invention, there is provided a process for the preparation of perhaloalkanoyl chloride which comprises contacting 1,1,1-trichloroperhaloalkane with an effective amount of a sulfur trioxide-containing substance selected from the group consisting of oleum, $SO_3$ and stabilized $SO_3$ in the presence of a catalytic amount of a halogen catalyst, wherein the 1,1,1-trichloroperhaloalkane is a straight or branched chain acyclic organic compound having 2 to 8 carbon atoms and having at least one trihalomethyl group wherein at least one halo atom is fluorine and having the remaining carbon atoms substituted by F, Cl, Br or I atoms.

DETAILED DESCRIPTION OF THE PRESENT INVENTION AND OF THE PREFERRED EMBODIMENTS

The present invention employs a catalytic amount of a non-metallic, halogen catalyst for the contact of 1,1,1-trichloroperhaloalkane with a sulfur trioxide containing substance for a time sufficient to effect conversion thereof to perhaloalkanoyl chloride. While toxic mercurial salts catalysts were disclosed in the U.S. Pat. No. 3,102,139, the halogen catalyst of the present invention is a member selected from the group consisting of iodine, bromine, iodine monochloride, iodine monobromide and bromine monochloride. Bromine is the preferred halogen catalyst. The catalytic amount of the halogen catalyst is in the range of from about 0.5% to about 10% by weight of 1,1,1-trichloroperhaloalkane. An upper limit on the catalytic amount of halogen catalyst has not been found to be critical; an amount of halogen catalyst as low as about 0.5% by weight of 1,1,1-trichloroperhaloalkane had been found effective. Only economic considerations would preclude employing catalytic amount of halogen catalyst in excess of about 10% by weight of 1,1,1-trichloroperhaloalkane.

The 1,1,1-trichloroperhaloalkane found useful in the present invention is a straight or branched-chain acyclic organic compound having 2 to 8 carbon atoms and having at least two trihalomethyl groups, with one trihalomethyl being 1,1,1 trichloromethyl and with the other trihalomethyl having at least one fluorine and having the remaining carbon atoms substituted by F, Cl, Br or I. Exemplary of the useful organic compounds are $FCX_2CCl_3$, $CF_3CX_2CCl_3$, $FCX_2(CX_2)_2-CCl_3$, $(FCX_2)_2CX-CX_2-CCl_3$ and $FCX_2(CX_2)_6CCl_3-(FCX_2)_2CX-(CX_2)_3CCl_3$, $$FCX_2(CX_2)_3-\underset{FCX_2-CX_2}{CXCCl_3} \text{ and } CF_3(CF_2)_6CCl_3,$$

wherein X is F, Cl, Br or I. While the trichloroperhaloalkanes may contain halogens such as chlorine at carbons other than the one carbon, for example $CF_2Cl-CCl_3$ (See Example IV) and $CF_2ClCFCl-CCl_3$ (See Example VI), substantially complete fluorine substitution at carbons other than carbon one is preferred; $CF_3(CF_2)_6CCl_3$ and $CF_3CCl_3$ are especially preferred.

The sulfur trioxide-containing substance useful in the present invention is a member selected from the group consisting of oleum, gaseous or liquid sulfur trioxide and stabilized liquid sulfur trioxide. Oleum is sulfuric acid with an amount of sulfur trioxide varying from a trace (so called fuming sulfuric acid) to 100% sulfur trioxide. Small amounts of compounds such as trimethoxy boraxime can conveniently be added to stabilize sulfur trioxide in the liquid form and prevent polymerization thereof to a solid. Stabilized liquid sulfur trioxide is the preferred sulfur trioxide containing substances. The amount of the sulfur trioxide-containing substance employed in the present invention is from about 1 mole to about 10 moles, preferably about 2 moles of sulfur trioxide per one mole of 1,1,1-trichloroperhaloalkane. Only economic considerations preclude employing more than 10 moles of sulfur trioxide per one mole of 1,1,1-trichloroperhaloalkane.

Operating temperatures and pressures for the preparation of perhaloalkanyl chloride are not critical. While operating temperatures in the range of about 20° to about 100° C. at pressures of about one atmosphere, plus or minus about 0.1 to 0.5 atmospheres have been found effective, as a matter of operating convenience temperatures in the range of about 25° to about 60° C. at a pressure of about one atmosphere are preferred.

Exact contact times are not critical. Preferred contact times vary between about 5 hours and about 24 hours for batch production of trifluoroacetylchloride; longer contact times result in higher percent conversion of 1,1,1-trichloroperhaloalkane to perhaloalkanoyl chloride. However, for continuous production, it is desirable to contact, in the temperature range of from about 20° to about 100° C., preferably from about 25° and 60° C. at about one atmosphere of pressure, 1,1,1-trichloroperhaloalkane with an effective amount of a sulfur trioxide-containing substance, preferably stabilized liquid sulfur trioxide in the presence of a catalytic amount of a halogen catalyst, preferably bromine, preferably in an amount of about 1% by weight of 1,1,1-trichloroperhaloalkane.

A cold trap provided on a reactor of any convenient design will allow collection of volatiles escaping from the contacting of the present invention. The perhaloalkanoyl chloride can conveniently be fractionally distilled. In a preferred embodiment, condensed volatiles from the contacting of 1,1,1-trichloro-2,2,2-trifluoroethane with $SO_3$ in the presence of $Br_2$ have been fractionally distilled for recovery of substantially pure, i.e., almost 100% pure, trifluoroacetyl chloride. The chemicals remaining in the reactor have also been fractionally distilled; starting materials, 1,1,1-trichloro-2,2,2-trifluoroethane, sulfur trioxide and halogen catalyst, i.e., bromine can conveniently be recycled for subsequent preparation of trifluoroacetyl chloride. Pyrosulfurylchloride, $S_2O_5Cl_2$, a by-product, can also be recycled as a convenient diluent.

The process of the invention will be further described and illustrated by the following specific examples.

GENERAL EXPERIMENTAL 1,1,1-trichloroperhaloalkanes are conveniently prepared by methods described in literature. See for example U.S. Pat. No. 3,102,139 which is hereby incorporated by reference. 1,1,1-trichloro-2,2,2-trifluoroethane is prepared in accordance with the following reactions:

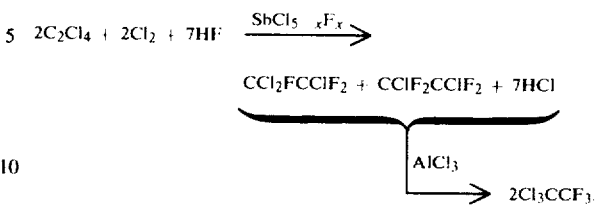

$CF_2ClCFClCCl_3$ is prepared by addition of $CCl_4$ to $CF_2=CFCl$ using $AlCl_3$ catalyst. 1,1,1-trichloroperhaloalkane having an even number of carbons, such as $CF_3(CF_2)_2CCl_3$ is prepared by reaction of a symmetrical ether, such as $(n-C_4F_9)_2O$ with $AlCl_3$ in an autoclave at 175° to 230° C. The trichloroperhaloalkane having an odd number of carbons, such as $CF_3(CF_2)_3CCl_3$ is prepared by reaction of an unsymmetrical ether, such as $CF_3(CF_2)_3OCF_2CF_3$ with $AlCl_3$ in an autoclave reaction at elevated temperatures.

EXAMPLE A

Preparation of $CCl_3CF_2CFClBr$ for Examples XXXI-XXXV $CF_2=CFCl$(18.4 g), $CCl_3Br$(80 mL) and acetyl peroxide (2.0 g) were shaken in a small autoclave for 12 hours at 100° C. to give unchanged olefin (10%), $CCl_3Br$ and a higher boiling fraction (65%) which was distilled to give pure $FClBrCCF_2CCl_3$.

EXAMPLE B

Preparation of $CCl_3CF_2CFClI$ for Examples XXXVI-XXXIX

In a manner similar to the above Example A, $CCl_3I$ was substituted for $CCl_3Br$ and pure $CCl_3CF_2CFClI$ was obtained.

EXAMPLE C

Preparation of $CCl_3CF_2CFClCF_2CFClBr$ for Examples XL-XLV $CF_2=CFCl$ (25 g), $CCl_3Br$ (25 g) and benzoyl peroxide (2.0 g) were shaken in a small autoclave for 18 hours at 100° C. to give mainly $CCl_3CF_2CFClCF_2CFClBr$.

EXAMPLE D

Preparation of $CCl_3CF_2CFClCF_2CFClCF_2CFClI$ for Examples Examples XLVI-L

In a manner similar to Example C hereinabove, $CCl_3I$ was substituted for $CCl_3Br$ and pure $CCl_3(CF_2CFCl)_3I$ was obtained.

Other 1,1,1-trichloroperhaloalkanes useful in the process of the present invention may be prepared in accordance with the directions of A. L. Henne et al. in J.A.C.S., 1951, Vol. 73, 5527-8 and J.A.C.S., 1954, Vol. 76, 1175-6 and of R. N. Haszeldine in J. Chem. Soc., 1953, 922-923 and 3565-3572.

EXAMPLE I

Into a 250 ml, 3-neck reaction flask equipped with a thermometer, magnetic stirring bar, dropping funnel and a water-cooled condenser, topped by a dry ice condenser maintained at −15° C. and connected to Dry Ice trap, cooled to −78° C., were charged 150 g (0.80 mole) of trifluorotrichloroethane ($CF_3CCL_3$) and 7.5 g bromine. At room temperature, 145 g (1.82 moles) of SO$_3$ were added over a half-hour period. The reaction mixture was heated from 25° C. to 60° C. over a twelve hour period. Fractional distillation of the cold trap product, (102.8 g), effected recovery of 85 g (0.64 mole) of trifluoroacetyl chloride (CF$_3$COCl), bp −19° C. Distillation of the material remaining in the reaction flask showed the presence of 20 g (0.15 mole) CF$_3$CCl$_3$, bp 46° C. and 110 g (0.52 mole) S$_2$O$_5$Cl$_2$, bp 153° C., as well as unreacted SO$_3$ and bromine catalyst. Thus of the starting material fed 80% was converted to CF$_3$COCl. The yield based on starting material consumed was 98%. The IR spectrum of the recovered trifluoroacetyl chloride was consistent with the expected structure.

EXAMPLE II

In the test apparatus as described in Example I, and following the procedure of Example I, 37.5 g (0.20 mole) of CF$_3$CCl$_3$, 100 g 65% oleum (0.80 mole as SO$_3$) and 3 g iodine were heated to reflux for 48 hours. Fractional distillation of the cold trap product, 19.3 g, effected recovery of 15.2 g (0.114 mole) of CF$_3$COCl for a 57.3% conversion. The yield based on recovery of 13 g (0.07 mole) CF$_3$CCl$_3$ starting material was 87%.

EXAMPLE III

In the test apparatus as described in Example I, and following the procedure of Example I, 37.5 g (0.20 mole) CF$_3$CCl$_3$, 100 g 65% oleum (0.80 mole as SO$_3$) and 3 g iodine monochloride were heated to reflux for 24 hours. Fractional distillation of the cold trap product, 15 g, effected recovery of 12 g (0.09 mole) of CF$_3$COCl for a 45% conversion. The yield based on recovery of 16 g (0.085 mole) of CF$_3$CCl$_3$ starting material was 78%.

EXAMPLE IV

In the test apparatus as described in Example I, and following the procedure of Example I, 150 g (0.74 mole) of CF$_2$ClCCl$_3$, 200 g 65% oleum (1.60 moles as SO$_3$) and 7.5 g bromine were heated from 25° C. to 60° C. over a 5 hour period. Fractional distillation of the cold trap product, 90 g, gave 77 g (0.375 mole) of CF$_2$ClCOCl, bp 26° C., for a 51% conversion.

EXAMPLE V

In the test apparatus as described in Example I, and following the procedure of Example I, 75 g (0.315 mole) of CF$_3$CF$_2$CCl$_3$, 100 g 65% oleum (0.80 mole as SO$_3$) and 5 g bromine were heated from 25° C. to 60° C. over a 5 hour period. Fractional distillation of the cold trap product, 50 g, gave 42 g (0.23 mole) of CF$_3$CF$_2$COCl, bp 9° C., for a 73% conversion.

EXAMPLE VI

In the test apparatus as described in Example I, and following the procedure of Example I, 135 g (0.50 mole) of CF$_2$ClCFClCCl$_3$, 150 g 65% oleum (1.20 moles as SO$_3$) and 10 g bromine were heated from 25° C. to 60° C. over a 5 hour period. Fractional distillation of the product gave 90 g (0.42 mole) CF$_2$ClCFClCOCl for an 84% conversion.

EXAMPLES VII–XXX

In the following examples the process of Example I is repeated in the apparatus as described except that the 1,1,1-trichloroperfluoroalkane reactant and catalyst are varied as indicated in Table 1.

TABLE 1

| | 1,1,1-trichloro-perhaloalkane | Catalyst | Product |
|---|---|---|---|
| VII | CF$_3$(CF$_2$)$_2$CCl$_3$ | Br$_2$ | CF$_3$(CF$_2$)$_2$COCl |
| VIII | " | I$_2$ | " |
| IX | " | ICl | " |
| X | " | IBr | " |
| XI | " | BrCl | " |
| XII | (CF$_3$)$_2$CF(CF$_2$)$_2$CCl$_3$ | Br$_2$ | (CF$_3$)$_2$CF(CF$_2$)$_2$COCl |
| XIII | " | I$_2$ | " |
| XIV | " | ICl | " |
| XV | " | IBr | " |
| XVI | " | BrCl | " |
| XVII | CF$_3$(CF$_2$)$_5$CCl$_3$ | Br$_2$ | CF$_3$(CF$_2$)$_5$COCl |
| XVIII | " | ICl | " |
| XIX | " | IBr | " |
| XX | " | BrCl | " |
| XXI | CF$_3$(CF$_2$)$_6$CCl$_3$ | Br$_2$ | CF$_3$(CF$_2$)$_6$COCl |
| XXII | " | I$_2$ | " |
| XXIII | " | ICl | " |
| XXIV | " | IBr | " |
| XXV | " | BrCl | " |
| XXVI | FCCl$_2$(CFCl)$_6$CCl$_3$ | Br$_2$ | FCCl$_2$(CFCl)$_6$COCl |
| XXVII | " | I$_2$ | " |
| XXVIII | " | ICl | " |
| XXIX | " | IBr | " |
| XXX | " | BrCl | " |

EXAMPLES XXXI–L

In the following examples the process of Example I is repeated in the apparatus described except that the 1,1,1-trichloroperhalofluoroalkane reactant and catalyst are varied as indicated in Table 2.

TABLE 2

| Example | 1,1,1-trichloro-perhaloalkane | Catalyst | Product |
|---|---|---|---|
| XXXI | FClBrCCF$_2$CCl$_3$ | Br$_2$ | FClBrCCF$_2$COCl |
| XXXII | " | I$_2$ | " |
| XXXIII | " | ICl | " |
| XXXIV | " | IBr | " |
| XXXV | " | BrCl | " |
| XXXVI | FCllCCF$_2$CCl$_3$ | Br$_2$ | FCllCCF$_2$COCl |
| XXXVII | " | I$_2$ | " |
| XXXVIII | " | ICl | " |
| XXXIX | " | IBr | " |
| XL | " | BrCl | " |
| XLI | $\begin{array}{c}\text{Cl F}\\\text{| |}\\\text{F—CCF}_2\text{CCF}_2\text{CCl}_3\\\text{| |}\\\text{Br Cl}\end{array}$ | Br$_2$ | $\begin{array}{c}\text{Cl F}\\\text{| |}\\\text{F—CCF}_2\text{CCF}_2\text{COCl}\\\text{| |}\\\text{Br Cl}\end{array}$ |
| XLII | " | I$_2$ | |
| XLIII | " | ICl | " |

TABLE 2-continued

| Example | 1,1,1-trichloro-perhaloalkane | Catalyst | Product |
|---------|-------------------------------|----------|---------|
| XLIV    | "                             | IBr      | "       |
| XLV     | "                             | ICl      | "       |
| XLVI    | F—CCF$_2$CCF$_2$CCF$_2$CCl$_3$ with Cl, F, F on top and I, Cl, Cl on bottom | Br$_2$ | F—CCF$_2$CCF$_2$CF$_2$COCl with Cl, F, F on top and I, Cl, Cl on bottom |
| XLVII   | "                             | I$_2$    | "       |
| XLVIII  | "                             | ICl      | "       |
| XLIX    | "                             | IBr      | "       |
| L       | "                             | BrCl     | "       |

Although certain preferred embodiments of the present invention have been disclosed, for the purposes of illustration, it will be readily evident to one skilled in the art that various changes and modifications may be made therein without departing from the scope and spirit of the invention.

We claim:

1. A process for preparation of perhaloalkanoyl chloride, which comprises contacting a 1,1,1-trichloroperhaloalkane wherein the 1,1,1-trichloroperhaloalkane is a straight or branched chain acyclic organic compound having 2 to 8 carbon atoms and having at least one trihalomethyl group wherein at least one halo atom is fluorine and having the remaining carbon atoms substituted by F, Br Cl or I atoms with an effective amount of a sulfur trioxide-containing substance selected from the group consisting of oleum, SO$_3$ and stabilized SO$_3$ in the presence of a catalytic amount of a halogen catalyst.

2. The process of claim 1 wherein the halogen catalyst is a member selected from the group consisting of iodine, bromine, iodine monochloride, iodine monobromide and bromine monochloride.

3. The process of claim 1, wherein the halogen catalyst is iodine.

4. The process of claim 1, wherein the halogen catalyst is bromine.

5. The process of claim 1, wherein the halogen catalyst is iodine monochloride.

6. The process of claim 1, wherein the halogen catalyst is iodine monobromide.

7. The process of claim 1, wherein the halogen catalyst is bromine monochloride.

8. The process of claim 1 wherein the effective amount of the sulfur trioxide-containing substance contains from about one mole to about ten moles of sulfur trioxide to about one mole of 1,1,1-trichloroperhaloalkane.

9. The process of claim 1, wherein the catalytic amount of the halogen catalyst is in the range of about 0.5% to about 10% by weight of the 1,1,1-trichloroperhaloalkane.

* * * * *